United States Patent
Doll et al.

(10) Patent No.: US 9,511,213 B2
(45) Date of Patent: Dec. 6, 2016

(54) COUPLING FOR A MEDICAL INSTRUMENT

(75) Inventors: Frank Doll, Talheim (DE); Martin Hahn, Altheim (DE); Juergen Bogenschuetz, Altheim (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 84 days.

(21) Appl. No.: 12/476,751

(22) Filed: Jun. 2, 2009

(65) Prior Publication Data

US 2009/0297260 A1 Dec. 3, 2009

(30) Foreign Application Priority Data

Jun. 3, 2008 (DE) .......................... 10 2008 027 676

(51) Int. Cl.
*A61M 31/00* (2006.01)
*A61M 39/00* (2006.01)
(Continued)

(52) U.S. Cl.
CPC .............. *A61M 39/00* (2013.01); *F16L 37/23* (2013.01); *A61M 2039/1027* (2013.01); *Y10T 29/49826* (2015.01); *Y10T 403/599* (2015.01)

(58) Field of Classification Search
CPC ..................................................... F16L 37/23
(Continued)

(56) References Cited

U.S. PATENT DOCUMENTS 2,279,146 A * 4/1942 Schneller ...................... 285/277
2,505,093 A   4/1950 Brock
(Continued)

FOREIGN PATENT DOCUMENTS

DE   2913302 A1   11/1979
DE   7909593 U1   3/1983
(Continued)

OTHER PUBLICATIONS

European Search Report; EP 09 16 1703; Sep. 29, 2009; 3 pages.

*Primary Examiner* — Joshua Kennedy
(74) *Attorney, Agent, or Firm* — Whitmyer IP Group LLC

(57) ABSTRACT

A coupling for a medical instrument for connecting two lines, with a first coupling part, and with a second coupling part which can be inserted into the first coupling part in the longitudinal direction of the coupling parts. The coupling comprises first locking elements arranged on the first coupling part and second locking elements arranged on the second coupling part, the first locking elements being movable between a locking position, in which they engage with the second locking elements, and an unlocking position, in which they disengage from the second locking elements. The coupling further comprises retaining elements which are arranged on the first coupling part and which are movable between a retention position, in which they keep the first and second locking elements in engagement with each other, and a release position, in which the first and second locking elements can be disengaged. It is proposed that the first coupling part comprises a slide which is movable in the longitudinal direction thereof and which, upon insertion of the second coupling part into the first coupling part, is moved from an advanced position to a recessed position, that the slide is biased into the advanced position, and that sealing elements are arranged on an end of the second coupling part directed towards the first coupling part which in a state in which the first coupling part is connected to the second coupling part, seal off an interior of the coupling with respect to a fluid.

14 Claims, 2 Drawing Sheets

(51) Int. Cl.
*F16L 37/23* (2006.01)
*A61M 39/10* (2006.01)

(58) Field of Classification Search
USPC .......... 403/109.3, 187, 199, 318, 322.2, 325,403/377; 265/65.05; 285/316, 347, 388
See application file for complete search history.

(56) References Cited

U.S. PATENT DOCUMENTS

| | | | | |
|---|---|---|---|---|
| 2,646,994 | A * | 7/1953 | Scheiwer | 137/614.04 |
| 3,334,860 | A * | 8/1967 | Bolton, Jr. | F16L 37/23 251/149.1 |
| 3,407,847 | A * | 10/1968 | Snyder | 137/614.06 |
| 3,788,598 | A * | 1/1974 | German | F16L 37/38 251/149.6 |
| 4,198,080 | A * | 4/1980 | Carpenter | 285/277 |
| 4,289,414 | A * | 9/1981 | Recker | 403/12 |
| 4,402,626 | A * | 9/1983 | Recker | 403/328 |
| 4,949,745 | A * | 8/1990 | McKeon | 137/15.09 |
| 5,445,358 | A * | 8/1995 | Anderson | 251/149.6 |
| 5,452,736 | A * | 9/1995 | Arosio | 137/75 |
| 5,522,669 | A * | 6/1996 | Recker | 403/328 |
| 5,577,859 | A * | 11/1996 | Nau | 403/325 |
| 5,674,024 | A * | 10/1997 | Daumal Castellon | 403/321 |
| 5,709,243 | A * | 1/1998 | Wells et al. | 137/614.03 |
| 5,820,291 | A * | 10/1998 | Lutz | 403/328 |
| 6,129,334 | A * | 10/2000 | Kuwabara | 251/149.6 |
| 6,131,961 | A * | 10/2000 | Heilmann | 285/316 |
| 6,485,214 | B2 * | 11/2002 | Schill | 403/13 |
| 6,511,100 | B1 * | 1/2003 | Le Clinche | 285/316 |
| 6,709,019 | B2 * | 3/2004 | Parrott et al. | 285/1 |
| 6,779,778 | B2 * | 8/2004 | Kuwabara | 251/149.9 |
| 6,890,004 | B2 * | 5/2005 | Naito | 285/93 |
| 6,920,810 | B1 * | 7/2005 | Thompson et al. | 81/177.85 |
| 7,503,721 | B2 * | 3/2009 | Kuratomi | 403/322.2 |
| 7,938,456 | B2 * | 5/2011 | Chambaud et al. | 285/316 |
| 8,256,803 | B2 * | 9/2012 | Takahashi | 285/316 |
| 8,469,406 | B2 * | 6/2013 | Takahashi | 285/316 |
| 8,596,689 | B2 * | 12/2013 | Simon et al. | 285/316 |
| 8,646,811 | B1 * | 2/2014 | Chang | 285/316 |
| 2002/0149200 | A1 | 10/2002 | Fumioka | |
| 2002/0197105 | A1 * | 12/2002 | Chiang | 403/322.2 |
| 2007/0252384 | A1 * | 11/2007 | Dickerson et al. | 285/89 |
| 2008/0290657 | A1 | 11/2008 | McKeon, III | |
| 2009/0110477 | A1 * | 4/2009 | Seger | 403/376 |
| 2009/0133451 | A1 * | 5/2009 | Standar | 70/174 |
| 2013/0292591 | A1 * | 11/2013 | Chang | 251/149.6 |

FOREIGN PATENT DOCUMENTS

DE 3934610 A1 4/1991
EP 0442310 A1 8/1991

* cited by examiner

COUPLING FOR A MEDICAL INSTRUMENT

BACKGROUND OF THE INVENTION

The invention relates to a coupling for a medical instrument for connecting two lines, with a first coupling part, and with a second coupling part which can be inserted into the first coupling part in the longitudinal direction of the coupling parts, with first locking elements arranged on the first coupling part and second locking elements arranged on the second coupling part, the first locking elements being movable between a locking position, in which they engage with the second locking elements, and an unlocking position, in which they disengage from the second locking elements, and also with retaining elements which are arranged on the first coupling part and which are movable between a retention position, in which they keep the first and second locking elements in engagement with each other, and a release position, in which the first and second locking elements can be disengaged.

The invention further relates to a method for producing a first coupling part.

The expression "line", for the purpose of the invention, refers to all types of tubular structures, but also to lines for electricity or light. Examples include lines for fluids, that is to say liquids or gases, such as for example flexible hoses or rigid pipes, instrument channels, and also electrical leads and light guides.

A coupling with the aforementioned structural features is known from German Utility Model DE 79 09 593 U1.

A coupling of the aforementioned type is generally used to connect two lines to each other. For this purpose, the first coupling part is or can be connected to a first line, and the second coupling part to a second line.

However, one of the two lines to be connected to each other can also be an attachment piece of a device, for example of a pump, in which case the first coupling part or the second coupling part is then secured or can be secured to the housing of the device.

An example of the use of the aforementioned coupling is for connecting an irrigation and/or suction hose to an irrigation and/or suction source for medical applications. For example, in surgical procedures, particularly in minimally invasive endoscope-assisted surgery, suction and/or irrigation instruments are used to irrigate the operating site and to remove liquids and/or tissues from the operating site. Such a suction and/or irrigation instrument is connected to the suction and/or irrigation source via a hose by means of the aforementioned coupling.

When the aforementioned coupling is used for a medical instrument, there are strict demands in particular on the ease of handling, its ability to be cleaned sufficiently and a compact size. It is desirable in particular for the two coupling parts to be able to be plugged together simply in the longitudinal direction of the coupling parts and as far as possible without a rotational movement.

The coupling known from the abovementioned German utility model is likewise used in the medical field, for example in dialyzers or oxygenators for blood.

In the known coupling, the first locking elements arranged on the first coupling part are in the form of six balls which are distributed circumferentially in the wall of the first coupling part and which are movable substantially transverse to the longitudinal direction of the coupling, that is to say in the radial direction. The second locking elements formed on the second coupling part are in the form of a groove which is present on the outer circumference of the second coupling part and which is limited in the longitudinal direction by two annular flanges.

The retaining elements in the known coupling are formed by a longitudinally displaceable sleeve which is arranged on the first coupling part and surrounds the latter on the outside. To connect the first coupling part to the second coupling part, the second coupling part is inserted into the first coupling part until the groove comes to lie level with the balls. When inserting the second coupling part into the first coupling part, the outer sleeve of the first coupling part must be drawn back manually into the release position against the force of a spring bias and must be kept in this position in order to ensure that the balls can move into their unlocking position upon insertion of the second coupling part. It is only after complete insertion of the second coupling part into the first coupling part, that is to say when the balls lie level with the groove, that the sleeve can be let go, which sleeve then moves into the retention position, on account of the bias, and keeps the balls in engagement with the groove, as a result of which the two coupling parts are held together in the longitudinal direction.

In order to separate the known coupling, the reverse procedure is followed, that is to say the sleeve is first drawn back from the retention position to the release position, after which the second coupling part can then be pulled manually out of the first coupling part, or the first coupling part can be pulled manually from the second coupling part.

Although the two coupling parts of the known coupling can be connected to each other without a rotational movement, a disadvantage of the known coupling is that, particularly upon separation of the coupling, when the first coupling part is pulled off from the second coupling part, considerable force has to be applied manually in order to disengage the balls from the groove, whereby the coupling parts may catch during separation of the coupling, particularly if the sleeve is not maintained securely in its release position when the first coupling part is being pulled off from the second coupling part.

Moreover, the seal provided in this coupling is arranged such that it can be accessed only with difficulty.

An object of the invention is therefore to develop a coupling of the aforementioned type in such a way that the smooth running of the coupling is improved, particularly during separation.

A further aim is to improve the access to the seal in such a coupling.

A further aim is to make production of the first coupling part easier.

SUMMARY OF THE INVENTION

According to the invention, this object is achieved, with regards to the aforementioned coupling, by virtue of the fact that the first coupling part comprises a slide which is movable in the longitudinal direction thereof and which, upon insertion of the second coupling part into the first coupling part, is moved from an advanced position to a recessed position, that the slide is biased into the advanced position, and that sealing elements are arranged on an end of the second coupling part directed towards the first coupling part which, in a state in which the first coupling part is connected to the second coupling part, seal off an interior of the coupling with respect to a fluid.

The use of the term directed towards or away from the first or second coupling part relates in each case to the position of the coupling parts in the connected state.

According to the invention, the object is further achieved by a method for producing a first coupling part of a coupling for a medical instrument for connecting two lines, said method comprising the following steps:

providing a second part of a body of the first coupling part, which second part is tubular and has at least one first projection on its inner circumferential surface and, at an end directed towards the second coupling part, has at least one second projection on the outer circumferential surface, inserting an inner sleeve into the second part, wherein elastic elements are provided between a first section of the sleeve and the first projection of the second part, which elastic elements subject the sleeve to a force counter to the direction of insertion, arranging a safety device on the inner sleeve, wherein the safety device is mounted on the sleeve at a position downstream of the first projection of the second part in the direction of insertion, in order to prevent the sleeve falling out of the second part, providing locking elements in the second part, pushing an outer sleeve onto the second part, wherein the outer sleeve comprises a first section having a smaller internal diameter and a second section having a larger internal diameter, connecting a first part of the body to the second part, wherein the first part limits the movement of the outer sleeve in a direction counter to the direction in which it is pushed on, and wherein elastic elements are provided in the area of the second section between the outer sleeve and the first part, which elastic elements subject the outer sleeve to a force acting in the direction in which it is pushed on.

The slide provided in the coupling according to the invention, against which slide the second coupling part comes lie upon insertion into the first coupling part, and which is moved counter to the bias into a recessed position upon further insertion of the second coupling part, acts in the manner of an ejector to aid the separation of the second coupling part from the first coupling part, as a result of which the coupling can be separated with less manual force. As soon as the retaining elements have been moved to the release position for separating the coupling, the slide, biased into the advanced position, directly subjects the second coupling part to a force which acts in the direction of separation and which aids the separation of the first coupling part from the second coupling part, or the pulling of the second coupling part out of the first coupling part, according to the bias of the slide. Moreover, the slide provided according to the invention opens up the possibility of preferred embodiments in which the advantageous functions to be described below can be implemented.

By arranging the sealing elements on an end of the second coupling part directed towards the first coupling part, these elements can also be easily accessed by a user, for example ill order to replace them when signs of wear appear. Moreover, the interior of the coupling is protected from contamination by fluid. Moreover, a fluid present within the lines is also effectively protected from any sources of contamination possibly present in the coupling.

The method according to the invention for producing the first coupling part is distinguished by its particular simplicity, since most of the components can be connected simply by being pushed onto one another or, if appropriate, for example by being screwed or pressed onto one another, and the method also results in a coupling of particularly small size, which is also advantageous.

In a first preferred embodiment, the slide, in the advanced position, keeps the first locking elements in the unlocking position, and these keep the retaining elements in the release position.

This measure has a particular advantage when connecting and locking the two coupling parts to each other. Before the second coupling part is inserted into the first coupling part, the slide, by keeping the first locking elements in the unlocking position, and by these keeping the retaining elements in the release position, has the effect that, in order to connect the two coupling parts, the retaining elements do not first have to be moved by the user into the release position and kept there, as is the case in the known coupling in which the sleeve has to be drawn back and held in this retracted position by hand before the two coupling parts are connected. In the coupling according to the invention, in the aforementioned embodiment, the second coupling part simply has to be inserted into the first coupling part, or the first coupling part plugged onto the second coupling part, without the retaining elements having to be actuated. The further advantage of this measure is that the locking elements, particularly when they are designed as balls in the same way as in the known coupling, can be confined in their recesses in the wall of the first coupling part when the coupling parts are separated. In the known coupling, this is achieved by the fact that the pockets in which the balls are received narrow in the radially inward direction, but this has the disadvantage that the depth of penetration of the balls into the groove is small and, as a result, the axial force holding the coupling together in the connected state of the two coupling parts is low. In the present embodiment, therefore, locking elements in the form of balls can be freely movable in their seats in the first coupling part, that is to say the seats do not have to be designed tapering radially inwards, and this permits a greater depth of engagement of the balls in a correspondingly deeper groove and also a simpler production of the seats, which can be designed as cylindrical bores. For greater safety, however, a tapering, preferably in the form of a stepped bore, can also be provided. A stepped bore has the advantage of having a simple structure and of still providing a suitable depth of penetration.

In another preferred embodiment, the slide, in the recessed position, frees the first locking elements, such that these can come into engagement with the second locking elements, after which the retaining elements are movable from the release position to the retention position.

This measure too contributes advantageously to a further improved control of the movement of the locking elements between the locking position and the unlocking position, as a result of which the handling and in particular the smooth running of the coupling upon connection of the two coupling parts is improved, particularly if the retaining elements, as is proposed in another preferred embodiment, are biased into the retention position.

In another preferred embodiment, the bias of the slide is sufficient to eject the second coupling part from the first coupling part when the retaining elements are moved from the retention position to the release position.

In this embodiment, the slide provided according to the invention in the first coupling part advantageously acts as an ejector, as a result of which it is possible to separate the two coupling parts with very little manual force. In order to separate the two coupling parts, the retaining elements simply have to be moved from the retention position to the release position, as a result of which the locking elements are movable from the locking position to the unlocking position, such that the slide then presses the second coupling part out of the first coupling part.

In another preferred embodiment, the retaining elements, during the movement from the release position to the retention position, move the first locking elements from the unlocking position to the locking position.

The advantage of this is that the retaining elements not only keep the locking elements engaged or respectively free them in the release position, but also actively control the movement of the locking elements, as a result of which the operating safety of the coupling according to the invention is further improved.

In this connection, it is preferable if the first locking elements comprise at least one shaped body, preferably at least one ball, which is arranged in a wall of the first coupling part, and the retaining elements comprise a sleeve which surrounds the wall of the first coupling part and which comprises a first section of greater internal diameter and a second section of smaller diameter, with a run-on slope being present between the first and second sections.

This measure is an advantageous and structurally simple way of moving the first locking elements from the unlocking position to the locking position upon a movement of the retaining elements from the release position to the retention position. The run-on slope ensures advantageous and particularly smooth running of the locking mechanism.

In another preferred embodiment, the retaining elements are movable from the retention position to the release position by a movement in the longitudinal direction.

This measure has the advantage that only movements in the longitudinal direction of the coupling are needed to separate the coupling, which corresponds to the direction of connection and separation of the two coupling parts.

According to the aforementioned embodiment, the first and second section of the sleeve are advantageously arranged one after the other in the longitudinal direction, and the run-on slope extends in the longitudinal direction.

As an alternative to this, however, it may be equally expedient and preferable if the retaining elements are movable from the retention position to the release position by a movement that takes place in the circumferential direction.

This measure has the advantage that the coupling can be made shorter in the longitudinal direction, since no space is needed for an axial path of movement of the retaining elements. However, a movement of the retaining elements in the circumferential direction does not mean that the two coupling parts have to be connected to each other by rotation. Rather, the coupling according to the invention is designed as a plug-type coupling in this embodiment too.

According to the aforementioned embodiment, and in a particularly simple structural configuration, the first and second sections are arranged one after the other in the circumferential direction, and the run-on slope extends in the circumferential direction.

In another preferred embodiment, the slide is designed in the form of a sleeve which is arranged inside the first coupling part and which is guided on an inner face of the first coupling part, with an abutment being provided for the sleeve in the advanced position.

This measure is a structurally very simple way of designing the slide for the aforementioned functions, in which the slide, by virtue of its design as a sleeve, does not in any way impair a flow of fluid through the coupling.

In another preferred embodiment, a front end of the slide is provided with a run-on slope.

This measure has the advantage that the slide, in its movement from the recessed position to the advanced position, can run onto the locking elements, and a blocking of the movement of the slide into the advanced position is thereby avoided, in so far as the slide is intended, as was described in one of the aforementioned embodiments, to keep the first locking elements in the unlocking position. The run-on slope can be straight, convex or concave.

In another preferred embodiment, the sealing elements comprise an O-ring which is arranged in an annular groove in the end of the second coupling part directed towards the first coupling part and which, in a state when the first coupling part is connected to the second coupling part, bears against an inner face of a bore in the first coupling part.

This embodiment represents a structurally very simple design of the sealing elements, which can also at the same time be produced at low cost. An O-ring fitted in this way can be easily removed by cutting it open or rolling it out of the groove and, for example, can be replaced by a new O-ring, which greatly simplifies the exchange of the sealing elements.

In one embodiment of the aforementioned method, the elastic elements comprise at least one compression spring.

Compression springs retain their elasticity over a long period of time, thereby ensuring that the force exerted by the elastic elements is also exerted in the long term.

In another embodiment of the abovementioned method, the locking elements comprise at least one ball which is displaceable in a direction transverse to the longitudinal axis of the first coupling part.

This measure has the advantage that the use of balls is simple from the point of view of construction since they simply have to be fitted into a transverse bore, and that the round shape of the balls ensures particularly smooth running of a coupling part obtained according to the method.

In another embodiment of the aforementioned measure, the first projection is an annular bead and/or the second projection is an annular flange.

An annular bead and an annular flange are advantageous firstly because they can be easily formed during the production of the second part and secondly because they extend all round the inner and/or outer diameter of the second part. Therefore, during production of the coupling part, there are no problems in orienting the elastic elements with the second part, such that the production method is made considerably easier.

In another embodiment of the abovementioned method, the safety device is a nut which is screwed onto the inner sleeve.

The use of a nut as the safety device has the advantage that this can be easily connected to the second part, which greatly simplifies production.

Moreover, the use of a nut can permit a detachable connection, such that in this way a coupling part is obtained that can also be dismantled, for example for maintenance purposes. Moreover, when using such a nut, the latter can also be used to adjust the bias of the inner sleeve.

In another embodiment of the abovementioned method, the safety device is designed in one piece with the inner sleeve.

In this embodiment, which can be used as an alternative to the preceding one, the inner sleeve and the safety device form one component part. Here, the safety device can, for example, take the form of locking fingers which are arranged on the sleeve and which, for example, engage behind an annular bead provided on the inner circumferential surface of the second part. In this embodiment, the inserting of the sleeve and the mounting of the safety device form two stages of one working procedure in which the mounting of the safety device can, for example, consist in inserting the sleeve until the above-described locking fingers engage. This has the advantage that the method is made still more efficient in this way. This also has the advantage that the sleeve and the safety device can be produced inexpensively, e.g. as an injection moulded part.

The coupling according to the invention is preferably made of a biocompatible material and can be sterilized by steam, preferably also by gas and plasma, and can be cleaned and disinfected by chemicals and heat.

Further advantages and features will become apparent from the following description and from the attached drawings.

It will be appreciated that the aforementioned features and the features still to be explained below can be used not only in the respectively cited combination but also in other combinations or on their own, without departing from the scope of the present invention.

BRIEF DESCRIPTION OF THE DRAWINGS

The invention is described and explained in more detail below on the basis of a selected illustrative embodiment and with reference to the attached drawings, in which.

DETAILED DESCRIPTION OF A PREFERRED EMBODIMENT

Figure 1:
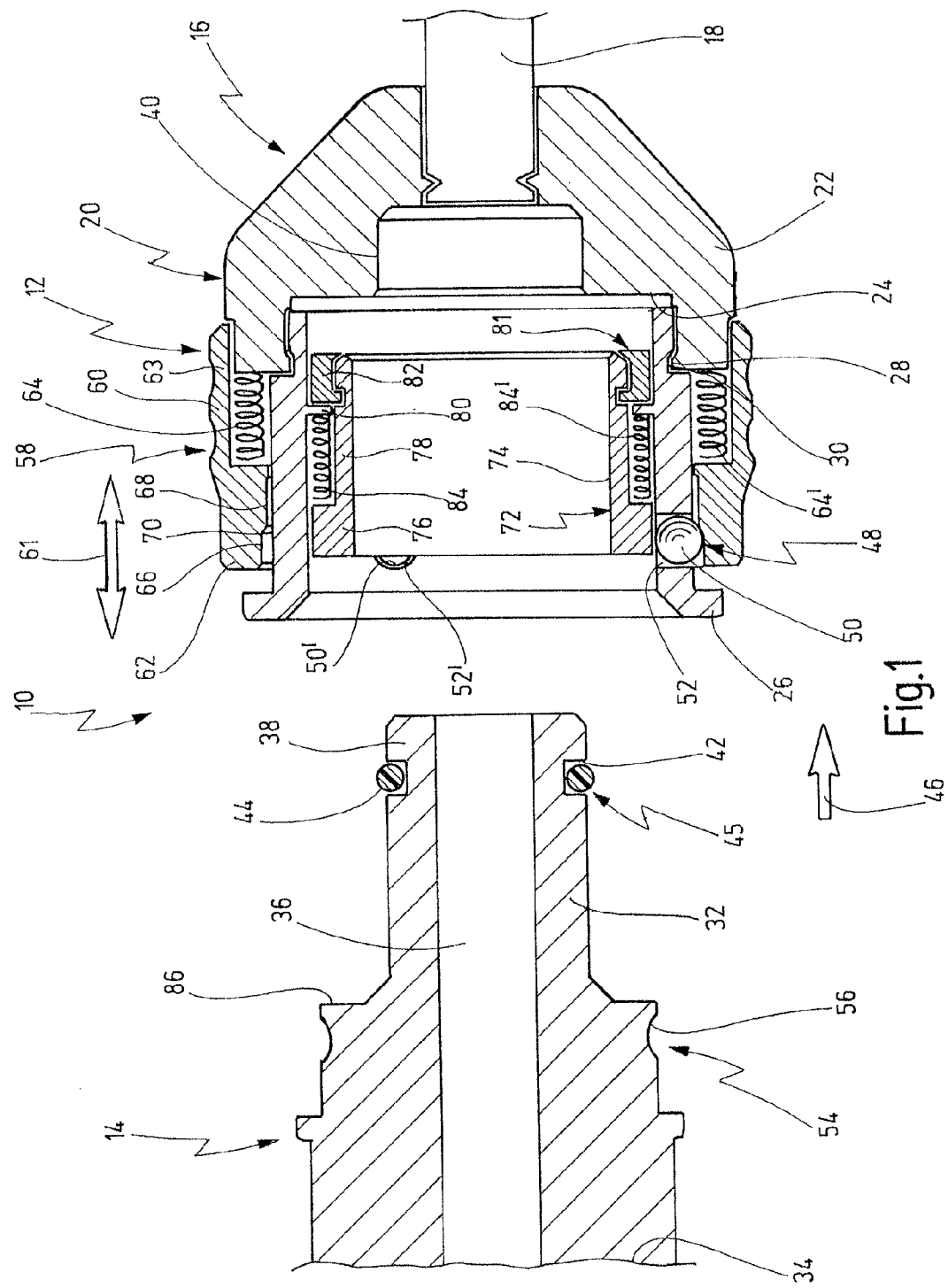
FIG. 1 shows a coupling according to the invention in longitudinal section, with the two coupling parts in the separated state.
Figure 2:
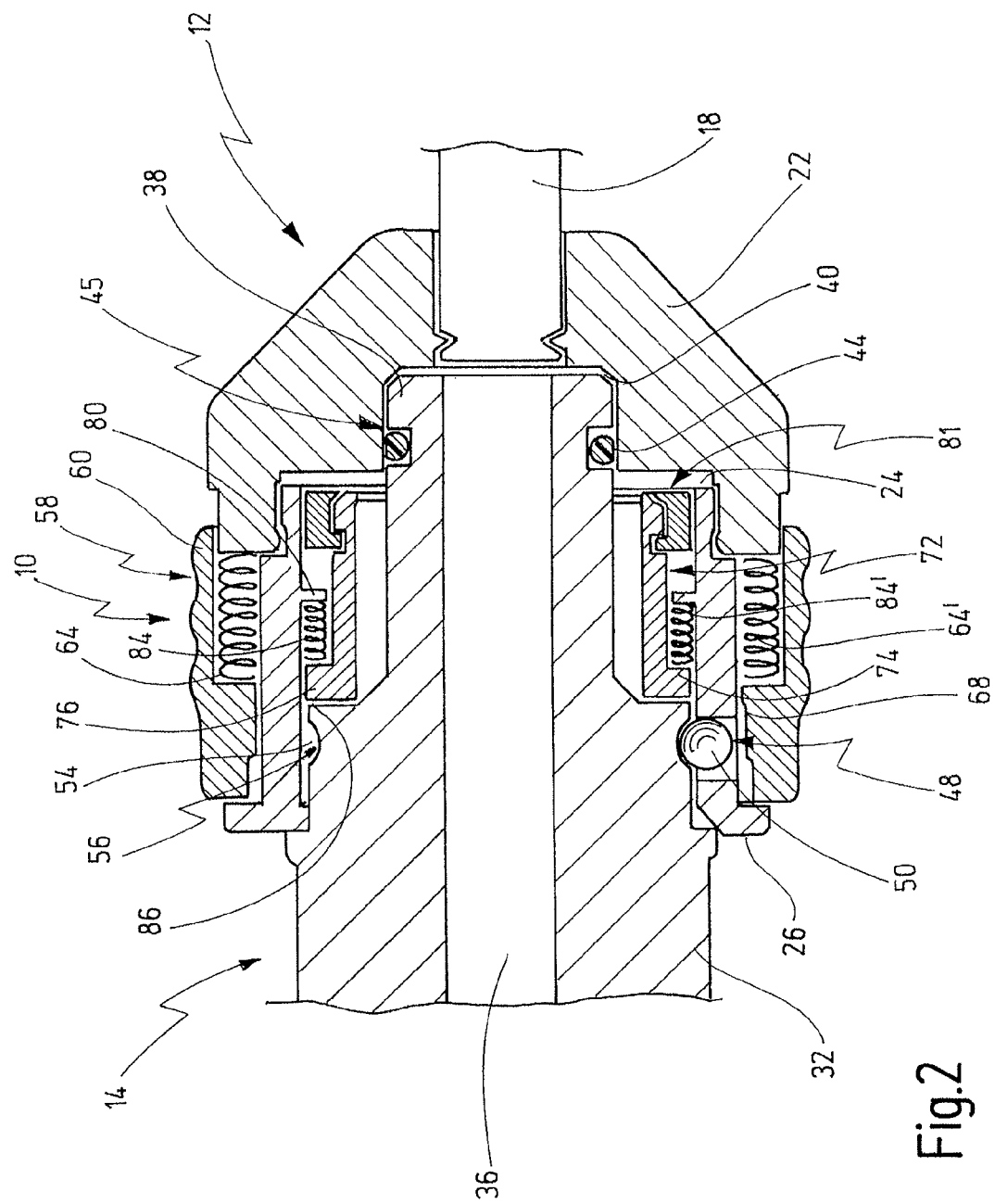
FIG. 2 shows the coupling from FIG. 1 in the connected state, in longitudinal section.

In FIGS. 1 and 2, a coupling for a medical instrument is designated in its entirety by reference number 10.

The coupling 10 comprises a first coupling part 12 and a second coupling part 14.

In the example shown, the first coupling part 12 is connected detachably at a rear end 16 to a hose 18. Here, an end of the hose 18 is screwed into the rear end 16 of the first coupling part 12.

In the connected state, a liquid or a gas is conveyed through the coupling 10, or a medical instrument is inserted through it.

The first coupling part 12 comprises a body 20, which is here composed of a first part 22 and of a second part 26. At an end directed towards the second coupling part 14, the first part 22 comprises a stepped bore 24. At the end of the stepped bore 24 directed towards the second coupling part 14, the first part 22 comprises an inner thread 28 that faces into the stepped bore 24. This inner thread 28 meshes with a corresponding outer thread 30, which is arranged on that end of the second part 26 of the body 20 directed away from the second coupling part 14, in the outer circumferential surface of the second part 26. In this way, the first part 22 and the second part 26 are screwed securely to each other.

The second coupling part 14 comprises a body 32 which, in the present case, is designed in one piece as a turning workpiece. At an end 34 of the body 32 directed away from the first coupling part 12, the second coupling part 14 in the present case is connected securely to a medical instrument (not shown here). A through-opening 36, e.g. for the passage of fluid, extends through the body 32.

At an end 38 of the body 32 directed towards the first coupling part 12, an annular groove 42 is formed in the outer circumferential surface of the body 32. An O-ring 44 made of an elastic material, for example of a rubber material, lies in this annular groove and here forms the sealing elements 45 of the second coupling part 14. The size of the O-ring 44 is thereby chosen such that it comes to lie securely in the annular groove 42. The external diameter of the end 38 of the body 32 corresponds approximately to the clear internal diameter of a second section 40 of the stepped bore 24 in the first part 22 of the body 20 of the first coupling part 12.

The second coupling part 14 can be inserted into the first coupling part 12 in the direction of the arrow 46, i.e. in the longitudinal direction of the coupling parts 12 and 14, in order to connect the first coupling part 12 to the second coupling part 14. FIG. 1 hereby shows the separated state of the coupling parts 12 and 14, while FIG. 2 shows the connected state of the two coupling parts 12 and 14.

First locking elements 48 are arranged on the first coupling part 12. In the present illustrative embodiment, the first locking elements 48 comprise three balls 50, 50'. The three balls 50, 50' are mutually offset by 120° in the circumferential direction, such that FIG. 1 shows only two, and FIG. 2 only one, of the three balls 50, 50'.

Instead of balls, the first locking elements 48 can also comprise other shaped bodies, for example pins or the like, but balls 50, 50' are preferred as first locking elements 48.

The balls 50, 50' are each received individually in pockets 52, 52' which are formed, in the second part 26 of the body 20 of the first coupling part 12, as radial through-bores extending transverse to the longitudinal direction in the wall of the second part 26. Corresponding to the three balls 50, 50', three such pockets 52, 52' are present in the first coupling part 12.

Instead of the through-bores shown here, the pockets can also be designed in the form of stepped bores which taper in the direction of the inner face of the second part 26 and thus prevent the balls 50, 50' from falling out.

In the pockets 52, 52', the balls 50, 50' are freely movable transverse to the longitudinal direction.

Second locking elements 54 are correspondingly arranged on the second coupling part 14. In the present illustrative embodiment, the second locking elements 54 comprise an annular groove 56. The annular groove 56 is formed all the way round in the outer circumferential face of the body 32 of the second coupling part 14. By virtue of the annular groove 56 being formed all the way round the circumference, the second coupling part 14 can be connected to the first coupling part 12 independently of the orientation of the second coupling part 14 in terms of rotation relative to the first coupling part 12.

The balls 50, 50' are movable between an unlocking position, which is shown in FIG. 1 and in which they are located in a radially outer setting in the pockets 52, 52', and a locking position, in which they protrude radially inwards from the pockets 52, 52' and engage in the groove 56. The groove 56 has a concave shape corresponding to the configuration of the first locking elements 48 as balls 50, 50'.

Also arranged on the first coupling part 12 are retaining elements 58 comprising a sleeve 60, most of which is arranged around the second part 26 of the body 20 of the first coupling part 12. The retaining elements 58, i.e. in the present illustrative embodiment the sleeve 60, are movable (see the double arrow 61) between a release position, which is shown in FIG. 1 and in which the sleeve 60 is drawn back in the direction of the rear end 16 of the first coupling part 12, and a retention position, which is shown in FIG. 2 and in which the sleeve is pushed forwards from the rear end 16 of the first coupling part 12.

The sleeve 60 comprises a first section 62 with a smaller internal diameter and a second section 63 with a larger internal diameter. In the space formed between the inner circumferential surface of the second section 63 and the outer circumferential surface of the second part 26, compression springs are arranged which, by way of example, are designated by reference numbers 64, 64'. Although a plurality of compression springs 64, 64' are shown in the present example, it is also possible to use a single compression spring which, for example, extends helically around the outer circumferential surface of the second part 26.

At one end, the compression springs 64, 64' bear against the first part 22 of the first coupling part 12 and, at the other end, they bear against the sleeve 60, such that the sleeve is biased into the advanced position shown in FIG. 2. In FIG. 1, in which the sleeve 60 is drawn back into the release position, the springs 64, 64' are correspondingly tensioned.

At its end directed towards the second coupling part 14, the sleeve 60 comprises a first section 66 having a larger internal diameter and, adjoining the latter in the longitudinal direction towards the free end 16, a second section 68 having a smaller internal diameter. The first section 66 and the second section 68 are connected to each other via a run-on slope 70, which extends in the longitudinal direction of the coupling 10.

A slide 72 is arranged inside the first coupling part 12, more precisely inside the second part 26. The slide 72 is designed in the form of a sleeve 74. This sleeve 74 comprises a first section 76, which has an external diameter corresponding approximately to the internal diameter of the second part 26 in this area, such that the sleeve 74 is guided via the first section 76 on the inner face of the first coupling part 12.

The slide 72 is movable longitudinally (see the double arrow 61) between an advanced position shown in FIG. 1 and a recessed position shown in FIG. 2. In order to limit the path of movement of the slide 72 in the form of the sleeve 74 longitudinally, in the direction of the arrow 46, the second part 26 has, on its inner surface, an annular bead 80 whose internal diameter corresponds approximately to the external diameter of a second section 78 of the sleeve 74 and which is smaller than the external diameter of the first section 76 of the sleeve 74. This design further improves the guiding of the sleeve 74 in the first coupling part 12.

In order to prevent the sleeve from falling out of the second part 26, a safety device 81 in the form of a nut 82 is mounted on that end of the slide 72 directed away from the second coupling part 14, the external diameter of the nut 82 corresponding approximately to the internal diameter of the second part 26 and being greater than the internal diameter of the annular bead 80. This prevents the sleeve 74 from being pulled out or falling out of the second part 26.

The slide 72 is also biased towards the position shown in FIG. 1 by compression springs, which are here designated by reference numbers 84, 84', for example, and which at one end bear against the annular bead 80 and at the other end bear against the first section 76 of the sleeve 74. In the position in FIG. 2, the compression springs 84, 84' are correspondingly tensioned. It is also clear here that, instead of a plurality of compression springs 84, 84', it is possible to use only a single compression spring which, for example, extends helically around the sleeve 74.

In the state shown in FIG. 1, the second coupling part 14 is separated from the first coupling part 12. In this state, the slide 72 is located in its advanced position, in which the slide 72 keeps the first locking elements 48 in their unlocking position, as a result of the first section 76 of the sleeve 74 of the slide 72 forcing the balls 50, 50' radially out into the pockets 52, 52'. Since the balls 50, 50' in the pockets 52, 52' are kept radially outwards by the slide 72 in FIG. 1, the retaining elements 58, i.e. in the present illustrative embodiment the sleeve 60, are also kept securely in their release position. When kept securely in their radially outer position, the balls 50, 50' prevent the sleeve 60 from moving past the balls 50, 50' with its run-on slope 70.

When the second coupling part 14 is now inserted into the first coupling part 12, the end face of a portion 86 of the body 32 of the second coupling part 14 comes into contact with the end face of the first section 76 of the sleeve 74 and, upon further insertion of the second coupling part 14 in the direction of the arrow 46, the slide 72 is moved into the recessed position according to FIG. 2. In this position, the slide 72 frees the first locking elements 48, here the balls 50, 50', which can come into engagement with the second locking elements 54 as soon as said second locking elements 54, here the groove 56, come to lie at the level of the first locking elements 48. This engagement of the first locking elements 48 with the second locking elements 54 takes place in the manner of a catch mechanism in which the retaining elements 58 in the form of the sleeve 60 press the balls 50, 50' actively into the groove 56 via the run-on slope 70. The retaining elements 58 move automatically into the retention position under the effect of the bias of the sleeve 60.

It will be clear from the above description that, in order to connect the first coupling part 12 to the second coupling part 14, the first coupling part 12 simply has to be plugged onto the second coupling part 14, or the second coupling part 14 simply has to be inserted into the first coupling part 12, and that the locking and retention of the coupling 10 then occurs completely automatically by means of the slide 72 in the manner of a catch mechanism. In contrast to the prior art, upon displacement of the two coupling parts, the retaining elements 58 do not have to be moved manually into the release position and held securely in said position, since this is done by the slide 72 in its advanced position.

In the connected state, the O-ring 44 bears on the inner wall of the second section 40 of the stepped bore 24, as a result of which the entire interior of the coupling 10 is sealed off against entry of any fluid that may be flowing through the hose 18 and the through-opening 36.

To separate the coupling 10, the procedure described below is followed, starting from the connected state shown in FIG. 2.

The retaining elements 58, here the sleeve 60, are moved back, counter to the bias, from the advanced retention position shown in FIG. 2 to the retracted release position shown in FIG. 1. Since the first section 66 of the sleeve 60 then comes to lie level with the balls 50, 50', the latter are now able to move radially outwards. Because of the bias of the slide 72 towards its advanced position shown in FIG. 1, it now pushes against the second coupling part 14 and, depending on the degree of bias of the slide 72, ejects the second coupling part 14 or at least aids a pulling force applied by the user, thereby making separation of the coupling 10 particularly easy to manage. As soon as the balls 50, 50' are disengaged from the groove, i.e. are located in their unlocking position, they are also maintained there, specifically first by the second coupling part 14. When the latter has been moved past the balls 50, 50' counter to the direction of the arrow 46 in FIG. 1, the first section 76 of the sleeve 74 of the slide 72 then keeps the balls 50, 50' in their unlocking position, such that the sleeve 60 can now already be let go. The slide 72 moves automatically into the advanced position shown in FIG. 1, after which the starting state according to FIG. 1 is once again reached in which the retaining elements 58 are kept in their release position and the first locking elements 48 in their unlocking position.

Whereas the retaining elements 58 in the illustrative embodiment shown here are movable from the retention position to the release position, and vice versa, in the longitudinal direction of the coupling, provision can also be made for this movement to be effected as a circumferential movement or rotational movement of the retaining elements 58 relative to the body 20 of the first coupling part 12. Accordingly, the first section 66 having a larger internal diameter and the second section 68 having a smaller internal diameter would then not be arranged one after the other in the longitudinal direction but instead one after the other in the circumferential direction, in which case the run-on slope 70 would extend in the circumferential direction.

The first coupling part 12 can be produced in the following way. First, the second part 26 of the body 20 of the first coupling part 12 is provided. The sleeve 74 is pushed axially into this second part 26 in the direction of the arrow 46, with the compression springs 84, 84' being introduced into the space formed between the outer circumferential surface of the second section 78 and the inner circumferential surface of the second part 26. In the next step, a safety device 81 in the form of a nut 82 is screwed onto the part of the sleeve 74 protruding rearwards past the annular bead 80, in order to form the safety device 81 for preventing the sleeve 74 from falling out of the second part 26 in the direction of the arrow 46. The nut 82 can also be used to regulate the bias of the compression springs 84, 84' and the position of the sleeve 74 in the second part 26.

In a second step, the balls 50, 50' are inserted into the pockets 52, 52', and the sleeve 60 is pushed on from outside over the second part 26, counter to the direction of the arrow 46. The compression springs 64, 64' are introduced into the space formed between the inner circumferential surface of the second section 63 of the sleeve 60 and the outer circumferential surface of the second part 26. Finally, in the same direction in which the sleeve 60 was pushed onto the second part 26, the portion of the first part 22 directed towards the second coupling part 14 is now pushed onto the portion of the second part 26 directed away from the second coupling part 14, with the inner thread 28 of the second part 22 being screwed onto the outer thread 30 of the second part 26. In this way, the finished first coupling part 12 is obtained which, in a further step, can be connected, for example by screwing, to a suction and/or irrigation hose or also directly to a medical instrument.

The first coupling part 12 can also be easily dismantled by carrying out the above steps in the reverse order, which greatly simplifies cleaning and maintenance of such couplings.

The whole coupling 10 is preferably sterilizable by steam, specifically also in the assembled state of the first coupling part 12. Furthermore, the whole coupling 10 is preferably made of biocompatible materials.

What is claimed is:

1. A medical system for connecting a first line to a second line via a coupling to transfer a fluid between the first line and the second line through said coupling, said medical system comprising:
    a first coupling part comprising a body, a slide which is movable in a longitudinal direction thereof, and a stepped bore having a large diameter portion and a small diameter portion, the first coupling part configured to be detachably connected to a first line located within the small diameter portion;
    a second coupling part which can be inserted into said first coupling part in the longitudinal direction of said coupling parts, the second coupling part comprising a body and a through-opening extending through the body, an external diameter of the body of the second coupling part corresponding with the large diameter of the stepped bore of the first coupling part, and an inner diameter of the through-opening corresponding to the smaller diameter portion;
    first locking elements arranged on said first coupling part;
    second locking elements arranged on said second coupling part, said first locking elements being movable between a locking position, in which they engage with said second locking elements, and an unlocking position, in which they disengage from said second locking elements;
    retaining elements which are arranged on said first coupling part and which are movable between a retention position, in which they keep said first and second locking elements in engagement with each other, and a release position, in which said first and second locking elements can be disengaged;
    at least one compression spring arranged between said body and said slide of said first coupling part, said at least one compression spring being in direct contact with said slide; and
    sealing elements which are arranged on an end of said second coupling part directed towards said first coupling part, said sealing elements comprising an O-ring which is arranged in an annular groove in an end of said second coupling part directed towards said first coupling part,
    wherein, upon insertion of said second coupling part into said first coupling part, said slide is moved from an advanced position to a recessed position;
    wherein said slide is biased into said advanced position by said at least one compression spring, and said slide contacts said first locking elements in said advanced position; and
    wherein said O-ring, which in a state in which said first coupling part is connected to said second coupling part, bears against an inner face of the stepped bore to seal off an interior of said coupling with respect to the fluid, such that the fluid is transferred through the coupling from the first line to the second line without the fluid penetrating into said first and second locking elements, said retaining elements, said slide and said at least one compression spring.

2. The medical system of claim 1, wherein said slide, in said advanced position, keeps said first locking elements in said unlocking position, and wherein these keep said retaining elements in said release position.

3. The medical system of claim 1, wherein said slide, in said recessed position, frees said first locking elements, such that these can come into engagement with said second locking elements, after which said retaining elements are movable from said release position to said retention position.

4. The medical system of claim 1, wherein said bias of said slide is sufficient to eject said second coupling part from said first coupling part when said retaining elements are moved from said retention position to said release position.

5. The medical system of claim 1, wherein said retaining elements, during a movement from said release position to said retention position, move said first locking elements from said unlocking position to said locking position.

6. The medical system of claim 5, wherein said first locking elements comprise at least one shaped body, which is arranged in a wall of said first coupling part, and wherein said retaining elements comprise a sleeve which surrounds said wall of said first coupling part and which comprises a first section having a larger internal diameter and a second section having a smaller internal diameter, with a run-on slope being present between said first and second sections.

7. The medical system of claim 6, wherein said retaining elements are movable from said retention position to said release position by a movement that takes place in the longitudinal direction.

8. The medical system of claim 7, wherein said first and second sections of said sleeve are arranged one after the other in the longitudinal direction, and wherein said run-on slope extends in the longitudinal direction.

9. The medical system of claim 6, wherein said at least one body is at least one ball.

10. The medical system of claim 1, wherein said retaining elements are movable from said retention position to said release position by a movement that takes place in the longitudinal direction.

11. The medical system of claim 1, wherein said slide is designed in the form of a sleeve which is arranged inside said first coupling part and which is guided on an inner face of said first coupling part, with an abutment being provided for said sleeve in said advanced position.

12. The medical system of claim 1, wherein the body of the first coupling part has a first body part and a second body part, the first body part having an inner thread that faces into the stepped bore and meshes with a corresponding outer thread arranged on the second body part to secure the first body part and second body part together.

13. The medical system of claim 12, wherein the O-ring bears against an inner face of the first body part of said first coupling part when the first coupling part and second coupling part are engaged with one another.

14. The medical system of claim 1, wherein said locking elements, said retaining elements and said slide are arranged beyond a location of the O-ring of the second coupling part which bears against said inner face of the stepped bore.

* * * * *